US010050471B2

(12) United States Patent
Krumme et al.

(10) Patent No.: US 10,050,471 B2
(45) Date of Patent: Aug. 14, 2018

(54) INDUCTIVE ROTARY JOINT WITH MULTIMODE INVERTER (71) Applicant: SCHLEIFRING GMBH, Furstenfeldbruck (DE)

(72) Inventors: Nils Krumme, Feldafing (DE); Ulrich Herrmann, München (DE)

(73) Assignee: SCHLEIFRING GMBH, Fürstenfeldbruck (DE)

(*) Notice: Subject to any disclaimer, the term of this patent is extended or adjusted under 35 U.S.C. 154(b) by 208 days.

(21) Appl. No.: 14/972,562

(22) Filed: Dec. 17, 2015

(65) Prior Publication Data
US 2016/0181871 A1 Jun. 23, 2016

(30) Foreign Application Priority Data

Dec. 18, 2014 (EP) .................................... 14198921

(51) Int. Cl.
A61B 6/03 (2006.01)
H01F 38/18 (2006.01)
H02J 5/00 (2016.01)
H05G 1/10 (2006.01)
H02J 50/10 (2016.01)
H02J 50/12 (2016.01)
(Continued)

(52) U.S. Cl.
CPC ............ H02J 50/10 (2016.02); A61B 6/03 (2013.01); H02J 5/005 (2013.01); H02J 50/12 (2016.02); H02M 3/335 (2013.01); H02M 3/3378 (2013.01); H01F 38/18 (2013.01); H02M 2001/0058 (2013.01); H05G 1/10 (2013.01); Y02B 70/1491 (2013.01)

(58) Field of Classification Search
CPC . A61B 6/03; A61B 6/032; H01F 38/18; H02J 5/005; H02J 17/00; H02J 50/10; H02J 50/12; H02M 3/335; H02M 3/3378; H02M 2001/0058; H05G 1/10; Y02B 70/1491
USPC ....................................................... 307/104
See application file for complete search history.

(56) References Cited

U.S. PATENT DOCUMENTS 5,671,128 A 9/1997 Nakamura et al.
7,054,411 B2 5/2006 Katcha et al.
(Continued)

FOREIGN PATENT DOCUMENTS

CN 1575759 A 2/2005
CN 1886810 A 12/2006
(Continued)

Primary Examiner — Levi Gannon
(74) Attorney, Agent, or Firm — Yakov S. Sidorin; Quarles & Brady LLP (57) ABSTRACT An inductive power transfer circuit or inductive rotary joint has an inductive rotating coupler with a primary side and a primary winding rotatably arranged against a secondary side and a secondary winding. The secondary side is connected via a rectifier to a load. The stray inductance of the coupler together with a resonance capacitor a series resonance circuit having a series resonance frequency. An inverter in a full bridge circuit is provided for converting a DC input voltage into an AC voltage. The inverter is operable in a full bridge mode to deliver a high power level and in a half bridge mode to deliver a low power level. This results in a broad dynamic range, soft power on and improved safety, as switching between the modes may be controlled by a simple hardware.

10 Claims, 4 Drawing Sheets (51) Int. Cl.
*H02M 3/335* (2006.01)
*H02M 3/337* (2006.01)
*H02M 1/00* (2006.01)

(56) References Cited

U.S. PATENT DOCUMENTS

| | | |
|---|---|---|
| 2004/0264642 A1 | 12/2004 | Katcha et al. |
| 2007/0195924 A1 | 8/2007 | Krumme |
| 2011/0285349 A1* | 11/2011 | Widmer ............... B60L 11/182 320/108 |
| 2014/0009109 A1* | 1/2014 | Lee ...................... H02J 17/00 320/108 |
| 2014/0268897 A1* | 9/2014 | Zimmanck ........ H02M 3/3353 363/17 |
| 2014/0300206 A1 | 10/2014 | Moes et al. |
| 2015/0062971 A1* | 3/2015 | Ye ..................... H02M 3/33569 363/17 |

FOREIGN PATENT DOCUMENTS

| | | |
|---|---|---|
| CN | 101431296 A | 5/2009 |
| CN | 102810913 A | 12/2012 |
| CN | 103208920 A | 7/2013 |
| EP | 2530805 | 1/2011 |

\* cited by examiner

INDUCTIVE ROTARY JOINT WITH MULTIMODE INVERTER

CROSS-REFERENCE TO RELATED APPLICATIONS

This application claims priority from and benefit of the European Application No. 14198921.0 filed on Dec. 18, 2014. The disclosure of this European Application is incorporated by reference herein.

BACKGROUND

1. Field of the Invention

The invention relates to an inductive power coupling device for coupling electrical power between two units that are rotatable against each other, specifically for power couplers used in computer tomography scanners. Such power couplers are also known as rotary joints.

2. Description of Relevant Art

In computer tomography (CT) scanners and other related machines high-power in the range from 10 kW up to more than 100 kW is transferred from a stationary side to a rotating side. There, a high voltage in the range of above hundred kilovolts is generated to produce x-ray radiation.

In U.S. Pat. No. 7,054,411 a multiple channel inductive rotary joint is disclosed. It has inductive channels for transferring power from the stationary side to the rotating side. There is an auxiliary power and a main power circuit. Furthermore a capacitive feedback link for power control is provided.

A contactless rotary joint with safety function is disclosed in EP 2 530 805 A1. The inverter of an inductively coupled rotary joint has two operating states. In a first operating state, it receives a three phase power line input. In a second operating state, it receives a single line power input. Depending on the input signal, a higher output voltage and a lower output voltage are generated at the secondary side, which may be used to distinguish between different operating states. The disadvantage is that high power contactors are required for switching over the input signal.

A general problem exists in all mentioned inductively-coupled rotary joints when switching the output power on. At the secondary side of the rotating transformer there are a rectifier and a filter capacitor. When the secondary side is switched off, the filter capacitor is discharged. For switching the secondary side on, the filter capacitor must be charged to the nominal output voltage. Without any current limiting means, there would be a very high current when starting the circuit, until the filter capacitor is charged. This may lead to a significant stress or even overload of associated electronic components.

SUMMARY

Embodiments of the invention provide a contactless inductively coupled rotary joint, which has a hardware safety circuit for delivering at least two different output power levels without requiring a high power contactor at the input side. A further problem to be solved is to provide an inductively coupled contactless rotary joint which is able to gradually increase the output power to avoid a large inrush current when switching the output power on. Another problem to be solved is to provide an inductively coupled contactless rotary joint having a significantly improved dynamic range.

Solutions of the problem are described in the independent claims. The dependent claims relate to further improvements of the invention.

The inductively coupled rotary joint has a primary side and a secondary side. It is preferred, if the primary side is the stationary side and the secondary side is the rotating side. If required, rotating and stationary sides may be switched, if power is to be transferred from the rotating side to the stationary side.

At the primary side, preferably a DC power is provided by a DC power source, having a positive output and a negative output, which may be a battery, a DC line, a rectifier like a bridge rectifier coupled to an AC line, or a power factor correction circuit coupled to an AC line. The DC power source supplies the DC power to an inverter circuit. The inverter circuit is basically a full-bridge circuit, also called H-bridge for generating an AC voltage. There are four semiconductor switches and four diodes, one diode in reverse direction parallel to one switch. The switches preferably are IGBTs or MOSFETs. Preferably, a control circuit is provided for generating control signals for the switches. The outputs of the inverter may be coupled via a resonance capacitor and an optional transformer and/or a common mode choke to the primary winding of the rotating transformer. These components preferably form a serious resonance circuit having a resonance capacitance and a resonance inductance. The resonance capacitance preferably is formed by the resonance capacitor. There may be other capacitors, preferably in a serious circuit, for example between the transformer and the primary winding or at the secondary winding. The resonance inductance preferably is formed by the stray inductance of either the transformer and/or the rotating coupler. The resonance capacitance and the resonance inductance determine at least one series resonance frequency. Energy coupled from the primary winding at the primary side is received by a secondary winding at the secondary side of the rotating transformer and is preferably fed to a rectifier. The rectifier delivers a rectified signal via a secondary filter capacitor to a secondary load. It may be a bridge rectifier or a voltage doubler circuit having diodes or controlled semiconductor switches like IGBTs or MOSFETs. If an AC voltage is required at the secondary side, the rectifier and capacitor may be omitted. The primary winding and/or the secondary winding may comprise a plurality of winding sections.

In a preferred embodiment, the inverter has at least two different operating modes which are most preferably set by the control circuit. In a first operating mode, the inverter is used as a half-bridge circuit, delivering only a lower power level to the secondary side, whereas in a second operating mode, the inverter is used as a full-bridge circuit delivering full power to the secondary side. For a smooth powering-on of the circuit, it is preferred that the inverter is working in a start sequence by starting in the first operating mode, delivering a lower power, and after some time switching to the second operating mode delivering full power. This avoids a large surge current at powering-on.

The inverter circuit comprises at least two switching branches having the following switches with diodes in parallel. A first branch includes a first switch, which is connected between the positive output of the DC power source and a first inverter output. It further includes a second switch, which is connected between the first inverter output and the negative output of the DC power source. A second branch includes a third switch, which is connected between the positive output of the DC power source and a second inverter output. It further includes a fourth switch, which is connected between the second inverter output and the negative output of the DC power source.

Preferably the inverter has a first operating mode, operating in a half bridge mode. In this mode one switch of one branch is closed, connecting an inverter output to either the positive output or the negative output of the DC power source. In the other branch the switches are closed alternatingly. The operation will be explained in an example. In this example, the fourth switch is closed, connecting the second inverter output to the negative output of the DC power source. The first and the second switches are closed alternatingly, connecting the first inverter output to the positive output or to the negative output of the DC power source. When connected to the positive output of the DC power source, energy is fed into the resonance circuit. When connected to the negative output of the DC power source, the resonance circuit is short-circuited. Therefore energy may only be delivered into the resonance circuit during the intervals where the first switch is closed. Generally the term closed as used herein relate to conductive or on states of semiconductor switches. The term open relates to isolating or off states of semiconductor switches.

For starting up the power supply, it is preferred to start in the half bridge mode. It is further preferred to operate the first branch of switches with a first frequency most preferably higher or lower than the resonance frequency. The fourth switch of the second branch is closed. When starting up the inverter, the resonance capacitor must get charged to a voltage corresponding to half of the voltage of the DC power source. To avoid a high charge current, it is preferred to start with low duty cycle of the first switch and increase this duty cycle with time until a certain power level is reached or until a maximum duty cycle of 50% whichever is lower. This way, there are short intervals during which power is delivered into the resonance circuit, providing a low power flow. When increasing the duty cycle, the intervals of power flow and therefore the transferred power increased. Preferably, the half bridge mode is initiated by independent and asynchronous depowering one of the drivers of one half bridge by a circuit independent from the bridge control circuit.

For further increasing the transfer of power by applying a higher primary voltage and thereby achieving a higher secondary voltage, preferably a transition to full bridge mode is made by alternatingly switching the first and second branch in a full bridge operation and by using a second frequency above or below the resonance frequency. Furthermore, it is preferred to adjust the duty cycle to obtain the required power transfer. The power transfer may also be controlled by adjusting the frequency which may be close to the resonance frequency. Preferably, the second frequency has a larger offset to the series resonance frequency than the first frequency. Most preferably, the second frequency is above the resonance frequency and the first frequency is slightly below the resonance frequency.

For reverting to the half bridge mode, the operating frequency may be maintained, but after the fourth switch has been closed permanently, the first and the second switches start operating with low duty cycle which is gradually increased.

By alternating between the half bridge mode and the full bridge mode, the inductively coupled rotary joint has a significantly improved dynamic range over prior art.

In a preferred embodiment and to implement a safety feature, a hardware circuit may be provided to switch between the half bridge mode and the full bridge mode. This may be done by a hardware circuit for disabling the full bridge mode operation by forcing one switch of a branch to an open state and the other switch of the same branch to a close state. This may simply be done by a switching transistor or by simple logic gates. This may work independently of the control signals of the switches as may be provided by the control circuit.

It is further preferred, if the secondary side has at least one means for evaluating the power delivered, and therefore for activating certain components like an X-ray tube, similar as disclosed in EP 2 530 805 A1 of the same applicant, which is herein included by reference. The safety circuit may simply block alternatingly switching of the switches of one branch by looking the first switch to an open position and a second switch to a close position. The other branch may operate normally. This forces the circuit to go into the half bridge mode, delivering only a reduced voltage level to the secondary side. There may be a further DC/DC converter at the secondary side to provide a controlled output voltage for certain electronic devices like control circuits and/or computers.

In a further embodiment, there is a DC/DC converter between the positive output and negative outputs and the load. This DC/DC converter may be an up-converter a down converter or a combination thereof. It also may be switchable between up—and down-conversion. Alternatively, there may also be a DC/AC converter.

Further embodiments relate to a method for switching and/or controlling the switches of the inverter as described above.

BRIEF DESCRIPTION OF THE DRAWINGS

In the following, the invention will be described by way of example, without limitation of the general inventive concept, on examples of embodiment and with reference to the drawings.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

Figure 1:
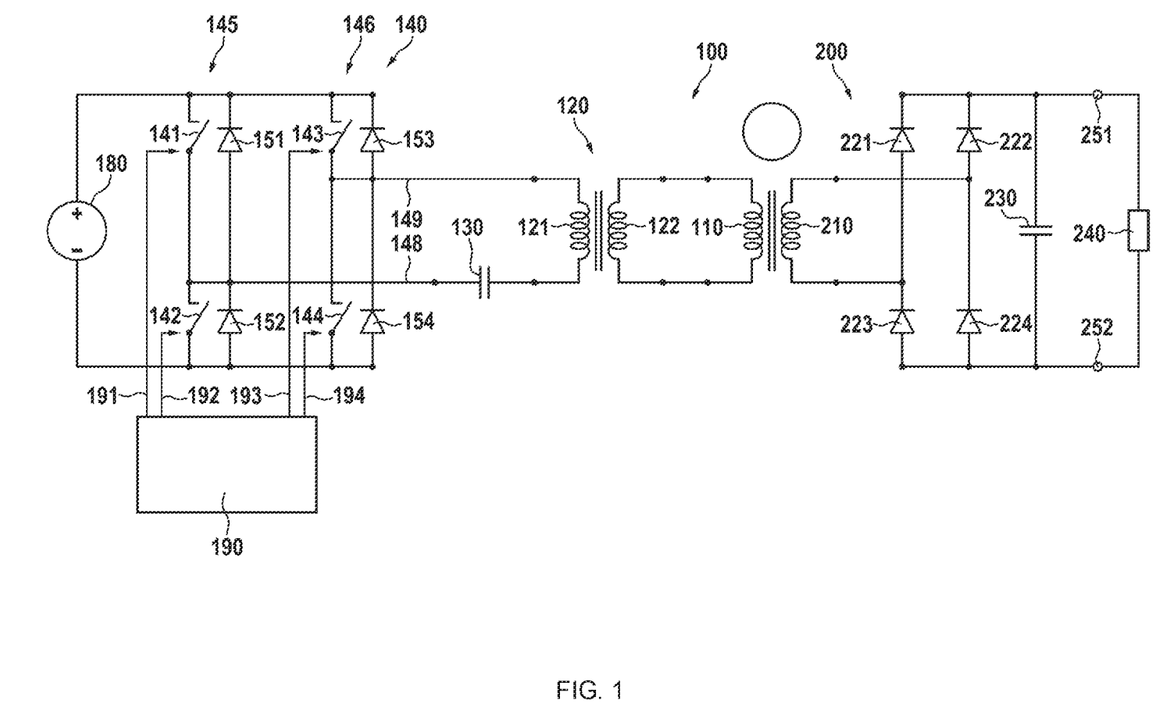
FIG. 1 shows a preferred embodiment.

In FIG. 1, the circuit diagram of a preferred embodiment is shown. An inductively coupled contactless rotary joint has a primary side 100 and a secondary side 200. Preferably, the primary side 100 is the stationary side, whereas the secondary side 200 is the rotating side. It is obvious that stationary and rotating sides may be exchanged for coupling power from the rotating to the stationary side. At the primary side, there is a DC power source 180 having a positive output and a negative output for delivering DC power to an inverter 140, which generates an AC signal which is further coupled via a resonance capacitor 130, an optional transformer 120 having a primary winding 121 and a secondary winding 122 to a primary winding 110 of the rotating transformer.

The DC power source 180 may be a battery, a DC line, a rectifier circuit like a bridge or a one-way rectifier for rectifying an AC power line signal or a power factor correction circuit for generating a DC signal from an AC power line. There may be additional filter capacitor (not shown in here) parallel to the DC power source 180.

The inverter 140 comprises a full bridge circuit with four switches 141, 142, 143, 144, whereas a first branch 145 is formed by a first switch 141 connected to the positive output of the DC voltage source and a second switch 142 connected to the negative output of the DC voltage source to provide a first inverter output 148. A second branch 146 is formed by a third switch 143 connected to the positive output of the DC voltage source and a fourth switch 144 connected to the negative output of the DC voltage source to provide a second inverter output 149. Furthermore, four diodes are provided. A first diode 151 is connected parallel to the first switch 141 in reverse direction. Second diode 152, third diode 153 and fourth diode 154 are connected in parallel to second switch 142, third switch 143, and fourth switch 144, all in reverse direction.

A control circuit 190 may be provided for generating control signals to control the switching state of the switches. It is preferred to have a first control signal 191 for controlling first switch 141, a second signal 192 for controlling second switch 142, a third control signal 193 controlling third switch 143, and a fourth control signal 194 for controlling fourth switch 144.

The outputs of the inverter coupled to a primary winding 110 of a rotating transformer, further having a secondary winding 210. It is further preferred to have a transformer 120 between the inverter output and the primary winding 110. This transformer may serve for voltage adapting and for isolation purposes. Furthermore, there is a resonance capacitor 130 collected in series with at least one of the inverter outputs. This resonance capacitor may also be located between the transformer and the primary winding or at the secondary winding. Alternatively, there may be a plurality of such capacitors.

At the secondary side, there is a secondary winding 210 of the rotating transformer delivering power via a bridge rectifier, comprising four diodes 221-224 via a secondary filter capacitor 230 to a load 240 being connected to a positive output 251 and a negative output 252. Instead of the bridge rectifier shown herein, any other kind of rectifier may be used, for example there may be a voltage doubler circuit. Alternatively, any controlled rectifier with active switches, like MOSFETs or IGBTs may be used instead of diodes.

Figure 2:
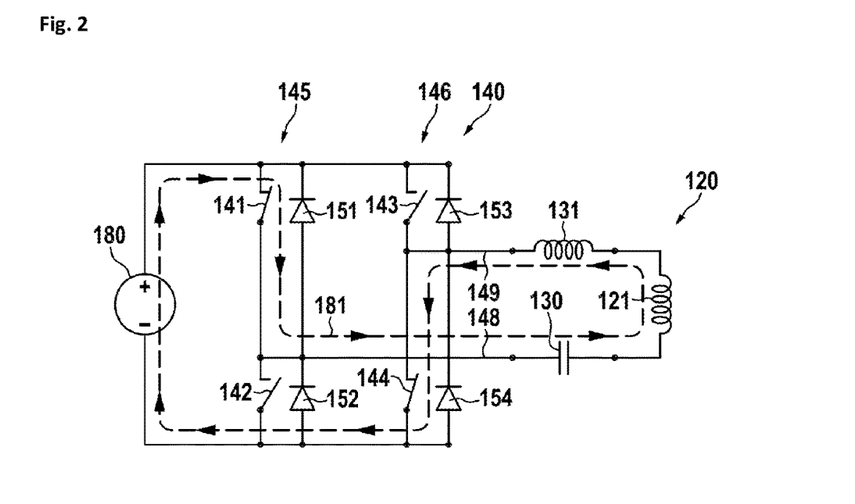
FIG. 2 shows a first state of the half-bridge operating mode.

In FIG. 2, a first state of the half-bridge operating mode is shown. Here, the remaining part of the circuit diagram at the right side (secondary side of transformer 120 including the secondary side) is not shown. Instead, a stray inductance 131 which may be part of transformer 120 and/or the rotating transformer 110, 210 is shown. This stray inductance 131 forms a series resonance circuit with the resonance capacitor 130. The resonance capacitor 130 preferably is at the position indicated, but it may also be at least partially between the transformer 120 and the primary winding 110 and/or in series with the secondary winding 210. Here, the first switch 141 and the fourth switch 144 are closed. The other switches are open. In this state, current is flowing through a first current path 181 from the power source 180 via first switch 141 into the resonance circuit comprising of resonance capacitor 130 and the stray inductance 131 including transformer 120 back through the fourth switch 144 to the DC power source 180. In this state, for a first half wave, energy is supplied from the DC power source 180 into the series resonance circuit and to the load.

Figure 3:
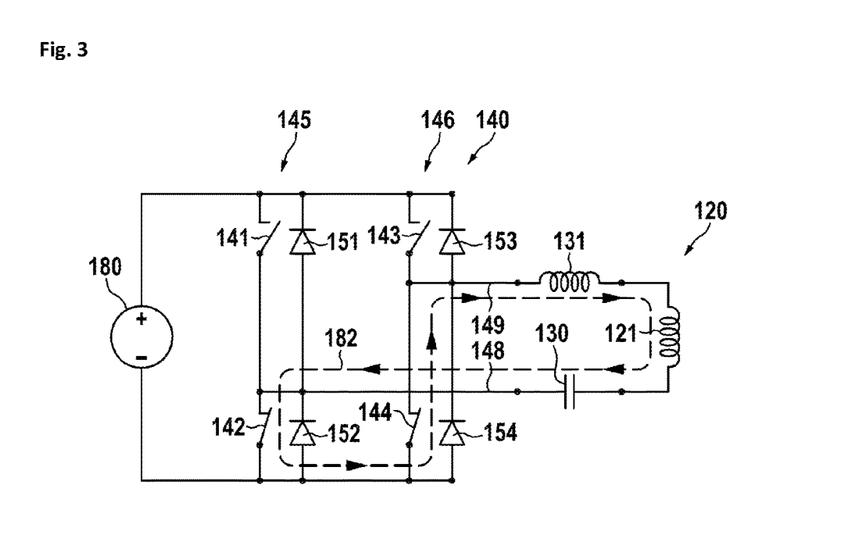
FIG. 3 shows a second state of the half-bridge operating mode

In FIG. 3, a second state of the half-bridge operating mode is shown. Here, the second switch 142 and the fourth switch 144 are closed. The other switches are open. Current is flowing through a second current path 182 from the resonance circuit comprising resonance capacitors 130 and stray inductance 131, including transformer 120 through the second switch 142 and the fourth switch 144 back to the resonance circuit. In this state, the series resonance circuit is short-circuited for a half wave.

Figure 4:
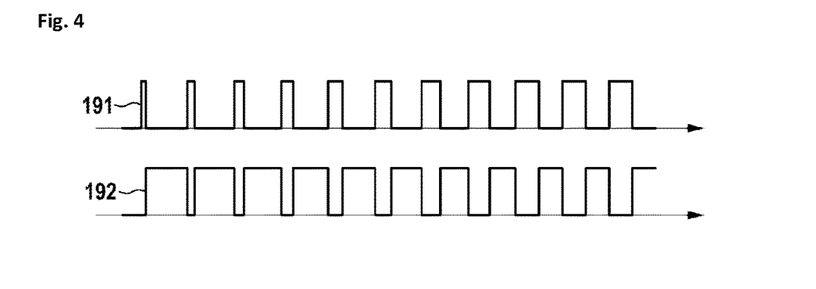
FIG. 4 shows the switch timing during a startup of the first mode.

In FIG. 4, the switch timing during a startup of the first mode is shown. The upper time line shows switch control signal 191 which controls the first switch 141. The lower time line shows switch control signal 192 controlling the second switch 142. During startup of a first half-bridge operating mode, the first switch 141 and the second switch 142 are alternatingly activated. The fourth switch 144 is always on, and the third switch 143 is always off. The high signal shows times, where the associated switch is activated or on. During the low states, the switch is off. During startup, the first switch 141 is activated with small pulses of signal 191 with increasing duration. Between the individual pulses is a pause preferably corresponding to the remainder of the period time of the operating frequency, which preferably is above the resonance frequency of the resonance circuit. Accordingly, during the pulses at the top line corresponding to on-times of the switch 141, the circuit is in a state as shown in FIG. 2, whereas it is in a state as shown in FIG. 3 during times where the pulses of the bottom line are high and switch 142 is on. Only during the on-times of the top diagram, when the first switch 141 is activated, energy is supplied into the resonance circuit. These times are increased continuously, until they are the same as the times in the bottom curve for the second switch 142. When this state is reached, the circuit is operating with a duty cycle of approximately 50:50. It is preferred to operate the circuit at a frequency slightly higher than the resonance frequency to get a lower power flow through the resonance circuit, as the series impedance of the series resonance circuit is higher than at its resonance frequency.

Figure 5A:
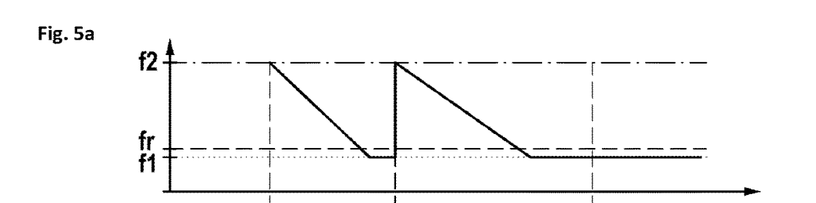
FIG. 5A, 5B, 5C show the frequencies and duty cycles of different operating modes.
Figure 5B:
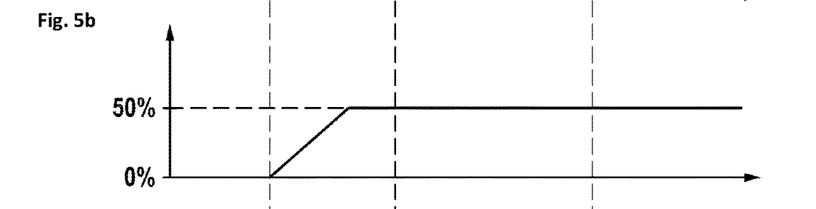

In FIG. 5b, the duty cycle curve 195 of the high side switch 141 is shown in different operating modes. At the first starting time 196, the circuit powers on from an off-state. It starts as previously explained with a very low duty cycle in half-bridge mode until a duty cycle of 50% or a lower required duty cycle is reached.

FIG. 5a describes the frequency which starts at a 2nd frequency f2 well above resonance frequency $f_r$ and is lowered to a first frequency f1 slightly below resonance frequency when normal operation of half bridge mode is reached.

Figure 5C:
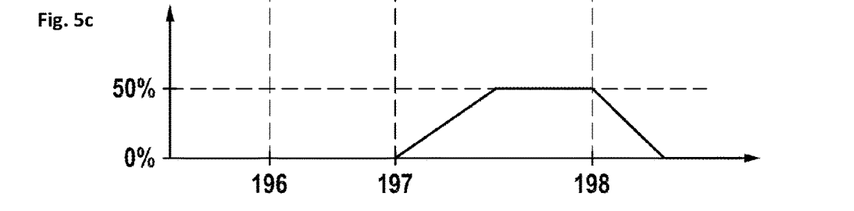

In FIG. 5c, the duty cycle curve 195 of the high side switch 141 is shown in different operating modes. During half bridge mode operation it is kept to zero.

At time 197, the inverter is switched to full-bridge mode. As this time, the frequency is increased back to f2 and the duty cycle of the high side switch 143 of the second half bridge is ramped up. During the half bridge operating mode, the average voltage at the resonance capacitor 130 is approximately half of the DC power source voltage. When switching over to a full-bridge mode of the circuit, the average voltage at the capacitor has to be decreased to zero. To prevent an excessive current flow, the operating frequency as shown in FIG. 5a of the circuit is increased to a frequency above the resonance frequency when switching over to a full-bridge mode, in which the first switch 141 is switched basically at the same time with the fourth switch 144, and second switch 142 is switched basically at the same time as third switch 143, alternating with the first and fourth switch.

At time 198, the power is again reduced and the inverter reverts to half-bridge mode. The frequency is the same as the previous full-bridge mode frequency, but the duty cycle of high side bridge (143, FIG. 5c) is ramped down from 50% to zero. Generally, if lower power is required, there may be also a lower duty cycle than 50% in the half-bridge mode or full bridge mode and frequency may be changed accordingly.

Figure 6:
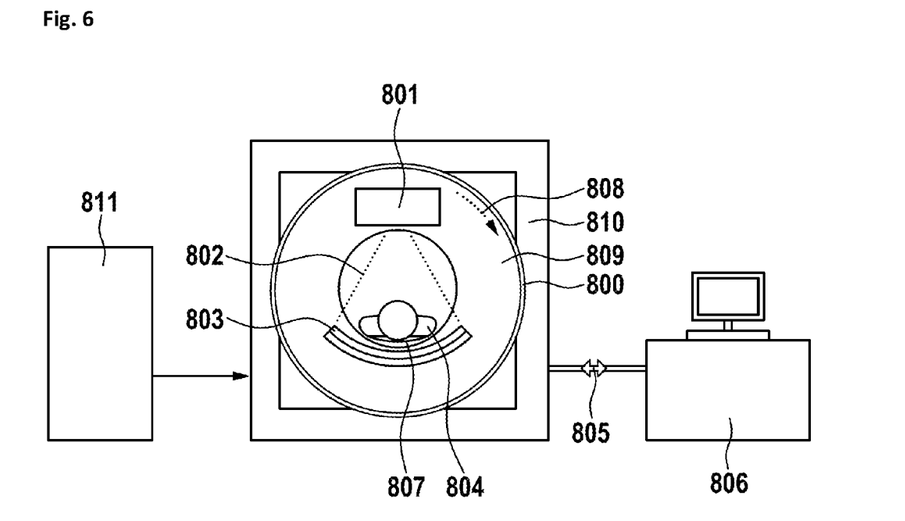
FIG. 6 shows schematically a CT (Computed Tomography) scanner gantry.

FIG. 6 shows schematically a CT (Computed Tomography) scanner gantry. The stationary part is suspended within a massive frame 810. The rotating part 809 of the gantry is rotatably mounted with respect to the stationary part and rotates along the rotation direction 808. The rotating part may be a metal disk which supports an X-ray tube 801, a detector 803 and further electronic and mechanic components. This disk may define a secondary ground. The X-ray tube is for generating an X-ray beam 802 that radiates through a patient 804 lying on a table 807 and which is intercepted by a detector 803 and converted to electrical signals and imaging data thereof. The data obtained by the detector 803 are transmitted via a contactless rotary joint (not shown) to an evaluation unit 806 by means of a data bus or network 805. Electrical power from a stationary power supply unit 811 may be transmitted by an inductive power coupler 800 to the rotating part. Other scanners like baggage scanners work in a similar way.

Modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

LIST OF REFERENCE NUMERALS

100 primary side
110 primary winding
120 transformer
121 primary winding
122 secondary winding
130 resonance capacitor
131 stray inductance
140 inverter
141 first switch
142 second switch
143 third switch
144 fourth switch
145 first branch
146 second branch
148 first inverter output
149 second inverter output
151-154 diodes
180 DC power source
181 first half-bridge current path
182 second half-bridge current path
190 control circuit
191-194 switch control signals
195 duty cycle
196 starting time
197 switch from half bridge to full bridge mode
198 revert to half bridge mode
200 secondary side
210 secondary winding
221-224 rectifiers
230 secondary filter capacitor
240 load
251 positive output
252 negative output
800 inductive power coupler
801 x-ray tube
802 x-ray beam
803 x-ray detector
804 patient
805 network
806 evaluation unit
807 patient table
808 rotation direction
809 rotating part
810 frame
811 power supply unit

The invention claimed is:

1. An inductive power transfer circuit comprising
an inductive rotating coupler having a primary side rotatably arranged against a secondary side, the primary side comprising at least a primary winding the secondary side comprising at least a secondary winding that is connected to a rectifier configured to deliver a DC output, the inductive rotating coupler further having a stray inductance;
a resonance capacitor coupled in series with at least one of the primary winding and secondary winding the resonance capacitor forming a series resonance circuit together with the stray inductance defining at least one series resonance frequency,
an inverter configured to convert a DC input voltage from a DC voltage source into an AC voltage, the inverter including at least four semiconductor switches that form
a first branch of a first switch and a second switch and a second branch of a third switch and a fourth switch in a full bridge circuit, and
a control circuit configured to generate control signals to control the at least four semiconductor switches, the control circuit being configured to generate control signals for a full bridge mode operation wherein alternatingly are closed the first switch together with the fourth switch, and the second switch together with the third switch,
wherein the control circuit is further adapted to generate control signals for a half bridge mode operation, in which one switch of one of the first and second branches is closed to connect an inverter output to either a positive output of the DC voltage source or a negative output of the DC voltage source, and switches of the other of the first and second branches are closed alternatingly, and wherein the half bridge mode operation is initiated by independent and asynchronous depowering of one of drivers of one half bridge by a circuit that is independent from a bridge control circuit, wherein the control circuit is adapted to generate control signals for the half bridge mode operation for a given time and to switch later to a full bridge mode operation, wherein the control signals start with a low-duty cycle, which is increased with time.

2. An inductive power transfer circuit according to claim 1, further comprising a transformer between the inverter and the primary winding.

3. An inductive power transfer circuit according to claim 1, wherein the control circuit is configured to perform the following before switching from the half bridge mode of operation to a full bridge mode of operation:
   to generate control signals for the half bridge mode of operation at a first frequency that is above a series resonance frequency by a first offset, and
   to change a frequency of the control signals to a second frequency that is below the series resonant frequency by a second offset, the second offset being smaller than the first offset.

4. An inductive power transfer circuit according to claim 1, wherein the control circuit is configured to perform the following before switching from the half bridge mode of operation to a full bridge mode of operation:
   to generate control signals for the half bridge mode of operation at a first frequency that is below a series resonance frequency by a first offset, and
   to change a frequency of the control signals to a second frequency that is above than the series resonant frequency by a second offset, the second offset being smaller than the first offset.

5. An inductive power transfer circuit according to claim 1, further comprising a hardware circuit configured to disable a full bridge mode operation by forcing one switch of a branch from the first and second branches to an open state and another switch of said branch to a closed state.

6. An inductive power transfer circuit according to claim 1, wherein the secondary side has at least one means for evaluating a delivered voltage and for activating auxiliary components upon a power state.

7. An inductive power transfer circuit according to claim 1, wherein a DC/DC converter is provided between a positive output, a negative output and a load.

8. A method for operating an inductive power transfer circuit that comprises
   an inductive rotating coupler having a primary side rotatably arranged against a secondary side, the primary side comprising at least a primary winding, the secondary side comprising at least a secondary winding connected to a rectifier configured to deliver a DC output, the inductive rotating coupler further having a stray inductance,
   a resonance capacitor coupled in series with at least one of the primary winding and the secondary winding, the resonance capacitor forming a series resonance circuit together with the stray inductance defining at least one series resonance frequency,
   an inverter configured to convert a DC input voltage from a DC voltage source into an AC voltage, the inverter comprising at least four semiconductor switches forming a first branch of a first switch and a second switch and a second branch of a third switch and a fourth switch in a full bridge circuit, the method comprising:
   in a full bridge mode, alternatingly switching the first switch together with the fourth switch and the second switch together with the third switch, and
   in a half bridge mode, switching one switch of one of the first and second branches to a closed state to connect an inverter output to either a positive output of the DC voltage source or a negative output of the DC voltage source, and alternatingly switching switches of another of the first and second branches to closed states,
   wherein the control circuit is adapted to generate control signals in the half bridge mode in a start sequence and to switch later to the full bridge mode,
   wherein the control signals start with a low duty cycle, which is increased with time.

9. A method according to claim 8, wherein for switching from the half-bridge mode to the full bridge mode, the switches are switched in the half bridge mode at a first frequency that is offset by a first value above the at least one series resonance frequency and then at a second frequency that is offset by a second value below the at least one series resonance frequency, the second value being smaller than the first value.

10. A method according to claim 9, wherein the first frequency is above the resonance frequency and the second frequency is further below the resonance frequency.

* * * * *